US011123435B2

(12) United States Patent
List et al.

(10) Patent No.: US 11,123,435 B2
(45) Date of Patent: Sep. 21, 2021

(54) TLR9 TARGETED THERAPEUTICS

(71) Applicants: H. Lee Moffitt Cancer Center and Research Institute, Inc., Tampa, FL (US); University of South Florida, Tampa, FL (US)

(72) Inventors: Alan List, Tampa, FL (US); Sheng Wei, Tampa, FL (US); Mark L. McLaughlin, Morgantown, WV (US)

(73) Assignees: H. Lee Moffitt Cancer Center and Research Institute, Inc., Tampa, FL (US); University of South Florida, Tampa, FL (US)

( * ) Notice: Subject to any disclaimer, the term of this patent is extended or adjusted under 35 U.S.C. 154(b) by 0 days.

(21) Appl. No.: 16/319,935

(22) PCT Filed: Aug. 2, 2017

(86) PCT No.: PCT/US2017/045140
§ 371 (c)(1),
(2) Date: Jan. 23, 2019

(87) PCT Pub. No.: WO2018/026943
PCT Pub. Date: Feb. 8, 2018

(65) Prior Publication Data
US 2019/0192669 A1 Jun. 27, 2019

Related U.S. Application Data
(60) Provisional application No. 62/370,428, filed on Aug. 3, 2016.

(51) Int. Cl.
*A61K 38/00* (2006.01)
*C07K 7/08* (2006.01)
*C12N 15/117* (2010.01)
*A61K 47/54* (2017.01)
*C07K 14/705* (2006.01)
*A61P 35/00* (2006.01)
*A61K 38/10* (2006.01)

(52) U.S. Cl.
CPC ............ *A61K 47/549* (2017.08); *A61K 38/00* (2013.01); *A61K 38/10* (2013.01); *A61P 35/00* (2018.01); *C07K 7/08* (2013.01); *C07K 14/70596* (2013.01); *C07K 2319/33* (2013.01); *C12N 15/117* (2013.01); *C12N 2310/17* (2013.01); *C12N 2310/3513* (2013.01); *C12N 2320/32* (2013.01)

(58) Field of Classification Search
None
See application file for complete search history.

(56) References Cited

U.S. PATENT DOCUMENTS

| | | |
|---|---|---|
| 5,135,917 A | 8/1992 | Burch |
| 5,168,053 A | 12/1992 | Altman et al. |
| 5,176,996 A | 1/1993 | Hogan et al. |
| 5,294,533 A | 3/1994 | Lupski et al. |
| 5,334,711 A | 8/1994 | Sproat et al. |
| 5,436,330 A | 7/1995 | Taira et al. |
| 5,476,766 A | 12/1995 | Gold et al. |
| 5,503,978 A | 4/1996 | Schneider et al. |
| 5,543,293 A | 8/1996 | Gold et al. |
| 5,580,737 A | 12/1996 | Polisky et al. |
| 5,580,967 A | 12/1996 | Joyce |
| 5,595,873 A | 1/1997 | Joyce |
| 5,616,466 A | 4/1997 | Cantor et al. |
| 5,624,824 A | 4/1997 | Yuan et al. |
| 5,627,158 A | 5/1997 | Cho-Chung |
| 5,631,115 A | 5/1997 | Ohtsuka et al. |
| 5,631,146 A | 5/1997 | Szostak et al. |
| 5,633,133 A | 5/1997 | Long et al. |
| 5,641,754 A | 6/1997 | Iversen |
| 5,645,985 A | 7/1997 | Froehler et al. |
| 5,646,020 A | 7/1997 | Swiggen et al. |
| 5,646,031 A | 7/1997 | DeYoung et al. |
| 5,646,042 A | 7/1997 | Stinchcomb et al. |
| 5,650,316 A | 7/1997 | Aggarwal et al. |
| 5,652,094 A | 7/1997 | Usman et al. |
| 5,652,107 A | 7/1997 | Lizardi et al. |
| 5,683,873 A | 11/1997 | George et al. |
| 5,683,874 A | 11/1997 | Kool |
| 5,683,902 A | 11/1997 | Hampel et al. |
| 5,688,670 A | 11/1997 | Szostak et al. |

(Continued)

FOREIGN PATENT DOCUMENTS

| | | |
|---|---|---|
| WO | 9203566 | 3/1992 |
| WO | 9322434 | 11/1993 |

(Continued)

OTHER PUBLICATIONS

SMCC and Sulfo-SMCC, ThermoScientific, accessed Mar. 23, 2020 at URL assets.thermofisher.com/TFS-Assets/LSG/manuals/MAN0011295_SMCC_SulfoSMCC_UG.pdf, 1 page (Year: 2020).*

(Continued)

*Primary Examiner* — Julie Ha
*Assistant Examiner* — Kristina M Hellman
(74) *Attorney, Agent, or Firm* — Thomas|Horstemeyer LLP

(57) ABSTRACT

Disclosed are compositions and methods for targeted treatment of cancers, such as TLR9-expressing cancers. In particular, molecules containing a TLR9 targeting ligand, such as a CpG oligodeoxynucleotide, that target lytic peptides to TLR9-expressing malignant cells are disclosed.

5 Claims, 11 Drawing Sheets
Specification includes a Sequence Listing.

(56) References Cited

U.S. PATENT DOCUMENTS

| | | |
|---|---|---|
| 5,691,317 A | 11/1997 | Cho-Chung |
| 5,693,535 A | 12/1997 | Draper et al. |
| 5,693,773 A | 12/1997 | Kandimalla et al. |
| 5,712,384 A | 1/1998 | Symonds et al. |
| 5,728,521 A | 3/1998 | Yuan et al. |
| 5,731,295 A | 3/1998 | Draper et al. |
| 5,731,424 A | 3/1998 | Toothman et al. |
| 5,770,715 A | 6/1998 | Sugiyama et al. |
| 5,780,228 A | 7/1998 | Parma et al. |
| 5,780,607 A | 7/1998 | Goodnow, Jr. et al. |
| 5,786,138 A | 7/1998 | Swenson |
| 5,786,462 A | 7/1998 | Schneider et al. |
| 5,792,613 A | 8/1998 | Schmidt et al. |
| 5,795,721 A | 8/1998 | Rabin et al. |
| 5,807,718 A | 9/1998 | Joyce et al. |
| 5,811,300 A | 9/1998 | Sullivan et al. |
| 5,834,185 A | 11/1998 | Ts'o et al. |
| 5,837,855 A | 11/1998 | Chowrira et al. |
| 5,846,713 A | 12/1998 | Pagratis et al. |
| 5,849,903 A | 12/1998 | Pietrzkowski et al. |
| 5,856,103 A | 1/1999 | Gray et al. |
| 5,856,188 A | 1/1999 | Hampel et al. |
| 5,856,463 A | 1/1999 | Prydz et al. |
| 5,858,660 A | 1/1999 | Eaton et al. |
| 5,861,254 A | 1/1999 | Schnieder et al. |
| 5,861,288 A | 1/1999 | Usman et al. |
| 5,864,026 A | 1/1999 | Jensen et al. |
| 5,866,701 A | 2/1999 | Hampel et al. |
| 5,869,246 A | 2/1999 | Matsuo et al. |
| 5,869,248 A | 2/1999 | Yuan et al. |
| 5,869,253 A | 2/1999 | Draper |
| 5,869,339 A | 2/1999 | Hampel et al. |
| 5,869,641 A | 2/1999 | Jayasena et al. |
| 5,874,566 A | 2/1999 | Veerapanane et al. |
| 5,877,021 A | 3/1999 | Stinchcomb et al. |
| 5,877,022 A | 3/1999 | Stinchcomb et al. |
| 5,877,162 A | 3/1999 | Werner et al. |
| 5,891,683 A | 4/1999 | Usman et al. |
| 5,891,684 A | 4/1999 | Usman et al. |
| 5,910,408 A | 6/1999 | Szostak et al. |
| 5,919,772 A | 7/1999 | Szyf et al. |
| 5,955,590 A | 9/1999 | Levina et al. |
| 5,962,426 A | 10/1999 | Glazer |
| 5,972,699 A | 10/1999 | Draper |
| 5,972,704 A | 10/1999 | Draper et al. |
| 5,985,621 A | 11/1999 | Usman et al. |
| 5,989,906 A | 11/1999 | Thompson |
| 5,989,908 A | 11/1999 | Scanlon |
| 5,990,088 A | 11/1999 | Ensoli et al. |
| 5,994,320 A | 11/1999 | Low et al. |
| 5,998,193 A | 12/1999 | Keese et al. |
| 5,998,203 A | 12/1999 | Matulic-Adamic et al. |
| 5,998,602 A | 12/1999 | Torrence et al. |
| 6,001,988 A | 12/1999 | Parma et al. |
| 6,005,095 A | 12/1999 | Capaccioli et al. |
| 6,007,995 A | 12/1999 | Baker et al. |
| 6,011,020 A | 1/2000 | Gold et al. |
| 6,013,443 A | 1/2000 | Heilig et al. |
| 6,013,522 A | 1/2000 | Monia et al. |
| 6,017,756 A | 1/2000 | Draper |
| 6,017,898 A | 1/2000 | Pietrzkowski et al. |
| 6,018,042 A | 1/2000 | Mett et al. |
| 6,020,130 A | 2/2000 | Gold et al. |
| 6,022,962 A | 2/2000 | Chowrira et al. |
| 6,025,198 A | 2/2000 | Bennett et al. |
| 6,028,186 A | 2/2000 | Tasset et al. |
| 6,030,776 A | 2/2000 | Eaton et al. |
| 6,033,910 A | 3/2000 | Monia et al. |
| 6,040,296 A | 3/2000 | Nyce |
| 6,046,004 A | 4/2000 | Wu et al. |
| 6,046,319 A | 4/2000 | Power et al. |
| 6,051,698 A | 4/2000 | Janjic et al. |
| 6,057,437 A | 5/2000 | Kamiya et al. |
| 2004/0023870 A1* | 2/2004 | Dedera ............... C07K 14/47 424/133.1 |
| 2008/0031887 A1 | 2/2008 | Lustgarten |
| 2013/0012437 A1 | 1/2013 | Yates et al. |
| 2014/0127241 A1 | 5/2014 | Leuschner et al. |
| 2015/0343078 A1 | 12/2015 | List et al. |

FOREIGN PATENT DOCUMENTS

| | | |
|---|---|---|
| WO | 9524489 | 9/1995 |
| WO | 9718312 | 5/1997 |
| WO | 9858057 | 12/1998 |
| WO | 9858058 | 12/1998 |
| WO | 0244321 | 6/2002 |
| WO | 2006052900 | 5/2006 |
| WO | 2010132622 | 11/2010 |
| WO | 2016070014 A1 | 5/2016 |
| WO | 2016070045 A1 | 5/2016 |

OTHER PUBLICATIONS

International Search Report for PCT/US2017/045140, dated Oct. 27, 2017.

Bernstein et al., Role for a bidentate ribonuclease in the initiation step of RNA interference, Nature, 409:363-6, 2001.

Carrara et al., Two helices plus a linker: A small model substrate for eukaryotic RNase P, Proc. Natl. Acad. Sci. (USA) 92:2627-2631, 1995.

Elbashir et al., RNA interference is mediated by 21-and 22-nucleotide RNAs, Genes Dev., 15:188-200, 2001.

Elbashir et al., Duplexes of 21-nucleotide RNAs mediate RNA interference in cultured mammalian cells, Nature, 411:494 498, 2001.

Fire et al., Potent and specific genetic interference by double-stranded RNA in Caenorhabditis elegans, Nature, 391:806-11, 1998.

Forster et al., External Guide Sequences for an RNA Enzyme, Science 238:407-409, 1990.

Hammond et al., An RNA-directed nuclease mediates post-transcriptional gene silencing in *Drosophila* cells, Nature, 404:293-6, 2000.

Hannon, RNA interference, Nature, 418:244-51, 2002.

Hurley et al., Covalent Binding of Antitumor Antibiotics in the Minor Groove of DNA. Mechanism of Action of CC-1065 and the Pyrrolo(1,4)benzodiazepines, Acc. Chem. Res., 19, 230-237, 1986.

Kohn, In Antibiotics III. Springer-Verlag, New York, pp. 3-11, 1975.

Krieg, Therapeutic potential of Toll-like receptor 9 activation, Nature Reviews, 5:471-484, 2006.

Martinez et al., Single-stranded antisense siRNAs guide target RNA cleavage in RNAi, Cell, 110:563-74, 2002.

Napoli, et al., Introduction of a Chimeric Chalcone Synthase Gene into Petunia Results in Reversible Co-Suppression of Homologous Genes in trans, Plant Cell 2:279-89, 1990.

Nykanen, et al., ATP requirements and small interfering RNA structure in the RNA interference pathway, Cell, 107:309-21, 2001.

Ui-Tei, et al., Sensitive assay of RNA interference in *Drosophila* and Chinese hamster cultured cells using firefly luciferase gene as target, Lett 479:79-82, 2000.

Yuan et al., Targeted cleavage of mRNA by human RNase P, Proc. Natl. Acad. Sci. USA 89:8006-8010, 1992.

Yuan et al., Substrate recognition by human RNase P: identification of small, model substrates for the enzyme, EMBO J 14:159-168, 1995.

Zhang et al, TLR9-mediated siRNA delivery for targeting of normal and malignant human hematopoietic cells in vivo, Blood, vol. 121, No. 8, p. 1304-1315 ,2013.

European Search Report issued for application 17837618.2, dated Apr. 17, 2020.

\* cited by examiner

TLR9 TARGETED THERAPEUTICS

This application claims benefit of U.S. Provisional Application No. 62/370,428, filed Aug. 3, 2016, which is hereby incorporated herein by reference in its entirety.

TECHNICAL FIELD

This application relates generally to compositions and methods for treating cancers, such as myelodysplastic syndromes (MDS).

BACKGROUND

Myelodysplastic syndromes (MDS) are hematopoietic stem cell malignancies with a rising prevalence owing to the aging of the American population. MDS comprise a group of malignant hematologic disorders associated with impaired erythropoiesis, dysregulated myeloid differentiation and increased risk for acute myeloid leukemia (AML) transformation. The incidence of MDS is increasing with 15,000 to 20,000 new cases each year in the United States and large numbers of patients requiring chronic blood transfusions. Ineffective erythropoiesis remains the principal therapeutic challenge for patients with more indolent subtypes, driven by a complex interplay between genetic abnormalities intrinsic to the MDS clone and senescence dependent inflammatory signals within the bone marrow (BM) microenvironment. Although three agents are approved for the treatment of MDS in the United States (US), lenalidomide (LEN) represents the only targeted therapeutic. Treatment with LEN yields sustained red blood cell transfusion independence accompanied by partial or complete resolution of cytogenetic abnormalities in the majority of patients with a chromosome 5q deletion (del5q), whereas only a minority of patients with non-del5q MDS achieve a meaningful response, infrequently accompanied by cytogenetic improvement. Although responses in patients with del5q MDS are relatively durable, lasting a median of 2.5 years, resistance emerges over time with resumption of transfusion dependence.

The available effective treatment options for patients with non-del(5q) is limited. Notably, MDS cases grow year over year due the increase in the American aging population and its combination. Frequently they are misdiagnosed leading to failure to treat serious infections or the wasting of expensive treatment and precious resources. Once a proper diagnosis is made patients have to rely on frequent blood transfusion and non-specific chemotherapy which have severe side effects and have limited benefit for patients with non-del(5q). The lack of effective treatment on MDS patients without del(5q) contributes to the enormous burden of this disease on both patient and caregivers and increases the risk of AML transformation. Therefore, there is definitely a need to develop a specific targeted therapeutic in this patient population.

SUMMARY

Compositions and methods are disclosed for targeted treatment of cancer or cancer-stem cells expressing a tumor antigen. In the disclosed compositions and methods, tumor antigen targeting agents, such as antibodies or ligands, are conjugated to a cytotoxic agent, e.g. via a bivalent linker. In some embodiments, the cytotoxic agent is a lytic peptide.

In some embodiments, the molecule comprises an anti-tumor associated antigen (TAA) binding agent conjugated to a lytic peptide, e.g. via a bivalent linker. In some embodiments, the lytic peptide comprises the amino acid sequence KAFKKAFKAFKKAFKAFK (SEQ ID NO:1). In some embodiments, the lytic peptide function is attributable to the alternating positively and negatively charged amino acids. Therefore, in some embodiments, the lytic peptide comprises the amino acid sequence PHH PPH HPH HPP HHP HHP (SEQ ID NO:2), where P is a positively charged amino acid and H is a hydrophobic amino acid. In some embodiments, the lytic peptide comprise an amino acid sequence that has at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to the amino acid sequence SEQ ID NO:2, or a fragment thereof of at least 12, 13, 14, 15, 16, 17, 18, 19, 20, 21, 22, 23, 24, or 25 amino acids in length.

In particular embodiments, compositions and methods are disclosed for targeted treatment of cancer or cancer-stem cells with extracellular toll like receptor-9 (TLR9) expression, such as primary human MDS progenitors, hematopoietic stem cell (HSC), and liver cancers. In some cases, the cancer comprises a solid tumor. In some cases, the cancer comprises a myelodysplastic syndrome (MDS). For example, the cancer can be non-del(5q) MDS. FIG. 4 identifies other cancers, such as lung, liver, and breast cancers, that have increased TLR9 expression. FIG. 5 shows TLR9 protein expression in a variety of tumor tissues. For example, cancers of the skin, esophagus, colon, rectum, liver, lung, and uterus have been shown to have increased TLR9 protein expression. In some cases, the method further involves assaying a biopsy sample from the subject for TLR9 expression prior to treatment.

In particular, molecules containing TLR9 targeting ligands that target lytic peptides to TLR9-expressing malignant cells are disclosed.

In some aspects, the TLR9 targeting ligand is an unmethylated CpG oligodeoxynucleotide, or an analogue or derivative thereof that binds TLR9. CpG oligodeoxynucleotides (or CpG ODN) are short single-stranded synthetic DNA molecules that contain a cytosine triphosphate deoxynucleotide ("C") followed by a guanine triphosphate deoxynucleotide ("G"). The "p" refers to the phosphodiester link between consecutive nucleotides, although some ODN have a modified phosphorothioate (PS) backbone instead. PS modification protects the ODN from being degraded by nucleases such as DNase in the body and poly G tail enhances cellular uptake.

The core CpG motif, which consists of a hexamer with a central unmethylated CpG, has the general formula RRCGYY (where R represents a purine and Y a pyrimidine). Early empirical structure-activity relationship (SAR) studies revealed species-specific differences in the optimal CpG motif, which is GTCGTT for humans. Besides the hexamer CpG motif, the immunestimulatory activity of an ODN is determined by the number of CpG motifs it contains (usually two to four are optimal), the spacing of the CpG motifs (usually at least two intervening bases, preferably thymine residues, is optimal), the presence of poly-G sequences or other flanking sequences in the ODN (effect depends on ODN structure and backbone), and the ODN backbone (a nuclease-resistant phosphorothioate backbone is the most stable and best for activating B cells, but gives relatively weaker induction of IFNα secretion from pDC compared with native phosphodiester linkages in the CpG dinucleotide). In addition, the immunestimulatory effects of the ODN are enhanced if there is a TpC dinucleotide on the 5' end and if the ODN is pyrimidine rich on the 3' side.

Numerous sequences have been shown to stimulate TLR9 with variations in the number and location of CpG dimers, as well as the precise base sequences flanking the CpG dimers. This led to the creation of five unofficial classes or categories of CpG oligonucleotides (ODN) based on their sequence, secondary structures, and effect on human peripheral blood mononuclear cells (PBMCs). The five classes are Class A (Type D), Class B (Type K), Class C, Class P, and Class S. A review of CpG oligonucleotides and their ability to bind TLR9 can be found in Krieg, A M. Nature Reviews 2006 5:471-484, which is incorporated by reference for these teachings. Example TLR9 agonist CpG ODNs include CPG 10101 (Coley), ODN 1018 ISS (Dynavax), CPG 7909 (GlaxoSmithKline (GSK)/Coley and DARPA/NIAID/Coley), ODN PF-3512676 (Pfizer/Coley), and ODN 1018 ISS (Dynavax).

In some cases, the TLR9 ligand comprises the CpG sequence TCCATGACGTTCCTGATGCT (SEQ ID NO:3). In some cases, the TLR9 ligand comprises the CpG sequence TCGTCGTTTTGTCGTTTTGTCGTT (SEQ ID NO:4). In some cases, the TLR9 ligand comprises the CpG sequence TCCATGACGTTCCTGACGTT (SEQ ID NO:5). In some cases, the TLR9 ligand comprises the CpG sequence GGGGACGACGTCGTGGGGGGG (SEQ ID NO:6). In some cases, the TLR9 ligand comprises the CpG sequence GGGGGACGATCGTCGGGGGG (SEQ ID NO:7). In some cases, the TLR9 ligand comprises the CpG sequence TCGTCGTTGTCGTTTTGTCGTT (SEQ ID NO:8). In some cases, the TLR9 ligand comprises the CpG sequence TCGACGTTCGTCGTTCGTCGTTC (SEQ ID NO:9). In some cases, the TLR9 ligand comprises the CpG sequence TCGCGACGTTCGCCCGACGTTCGGTA (SEQ ID NO:10). In some cases, the TLR9 ligand comprises the CpG sequence TCGTCGTTTTCGGCGCGCGCCG (SEQ ID NO:11). In some cases, the TLR9 ligand comprises the CpG sequence TCGTCGTCGTTCGAACGACGTTGAT (SEQ ID NO:12). In some cases, the TLR9 ligand comprises the CpG sequence TCGCGAACGTTCGCCGCGTTCG-AACGCGG (SEQ ID NO:13).

In some cases, some or all of the CpG nucleotides have phosphodiester backbones. However, in some embodiments, one or more of the nucleotides have modified phosphorothioate (nuclease resistant) backbones. For example, in some cases, the TLR9 ligand comprises the CpG sequence T*C*C*A*T*G*A*C*G*T*T*C*C*T*G*A*T*G*C*T* (SEQ ID NO:14, *=phosphorothioate). In some cases, the TLR9 ligand comprises the CpG sequence G*G*G*GACGACGTCGTGG*G*G*G*G*G* (SEQ ID NO:15, *=phosphorothioate). In some cases, the TLR9 ligand comprises the CpG sequence G*G*GGGACGATCGTCG*G*G*G*G*G* (SEQ ID NO:16, *=phosphorothioate). In some cases, the TLR9 ligand comprises the CpG sequence T*C*G*T*C*G*T*C*G*T*T*C*G*A*A*C*G*A*C*G* T*T*G*A*T* (SEQ ID NO:17, *=phosphorothioate).

In some embodiments, compositions and methods are disclosed for targeted treatment of cancer or cancer-stem cells with extracellular CD33 expression, such as acute myeloid leukemia (AML). In some embodiments, compositions and methods are disclosed for targeted treatment of cancer or cancer-stem cells with extracellular EGF-R expression, such as lung, head and neck, and many other epithelial cancers. In some embodiments, compositions and methods are disclosed for targeted treatment of cancer or cancer-stem cells with extracellular HER2 expression, such as breast cancers. In some embodiments, compositions and methods are disclosed for targeted treatment of cancer or cancer-stem cells with extracellular CD19 expression, such as B-cell Non-Hodgkin Lymphoma (NHL), Chronic lymphocytic leukemia (CLL), and B-cell Acute lymphoblastic leukemia (ALL). In some embodiments, compositions and methods are disclosed for targeted treatment of cancer or cancer-stem cells with extracellular CD123 expression, such as AML, blastic plasmocytoid dendritic cell neoplasm, hairy cell leukemia, and ALL. In some embodiments, compositions and methods are disclosed for targeted treatment of cancer or cancer-stem cells with extracellular B-cell maturation antigen (BCMA) expression, such as multiple myeloma. Tumor antigen targeting agents that bind CD33, EGF-R, HER2, CD19, CD123, or BCMA on tumor cells are known and can be used in the disclosed compositions and methods.

In some embodiments, the bivalent linker is a C6 amino-SMCC-Cys linker. In some embodiments, the linker is produced using click chemistry reactions. The click chemistry approach was originally conceived as a method to rapidly generate complex substances by joining small subunits together in a modular fashion. Various forms of click chemistry reaction are known in the art, such as the Huisgen 1,3-dipolar cycloaddition copper catalyzed reaction, which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

Also disclosed is a pharmaceutical composition comprising a molecule disclosed herein in a pharmaceutically acceptable carrier. Also disclosed is a method for treating a cancer, such as a TLR9-positive cancer, in a subject that involves administering to the subject a therapeutically effective amount of a disclosed pharmaceutical composition.

The cancer of the disclosed methods can be any cell in a subject undergoing unregulated growth, invasion, or metastasis that is expressing tumor antigen, such as TLR9, CD33, EGF-R, HER2, CD19, CD123, and BCMA. Thus, the cancer can be a sarcoma, lymphoma, leukemia, carcinoma, blastoma, or germ cell tumor. A representative but non-limiting list of cancers include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

In some cases, the cancer comprises a myelodysplastic syndrome (MDS). For example, the cancer can be non-del (5q) MDS. FIG. 4 identifies other cancers, such as lung, liver, and breast cancers, that have increased TLR9 expression. FIG. 5 shows TLR9 protein expression in a variety of tumor tissues. For example, cancers of the skin, esophagus, colon, rectum, liver, lung, and uterus have been shown to have increased TLR9 protein expression. In some cases, the method further involves assaying a biopsy sample from the subject for TLR9 expression prior to treatment.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
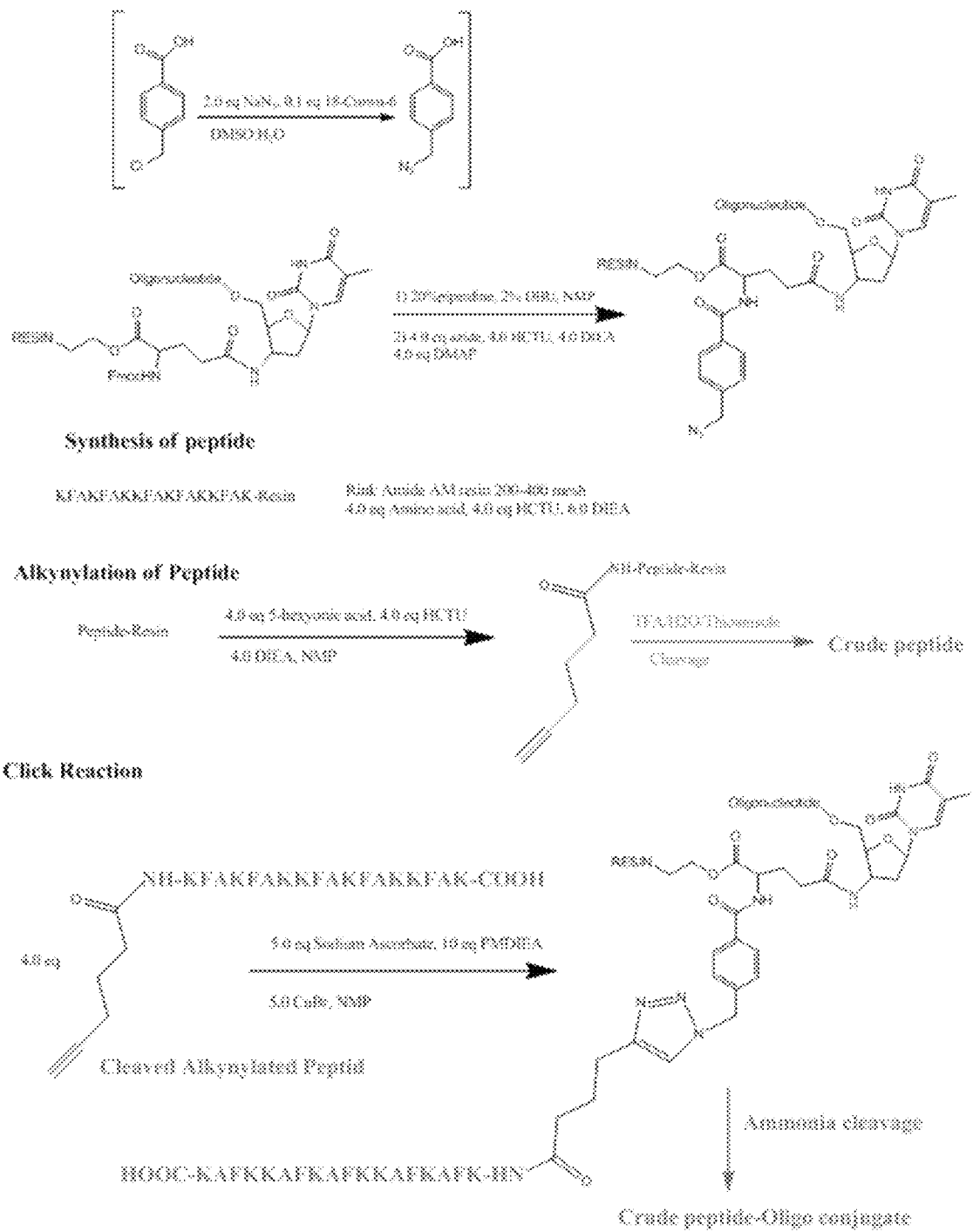
FIG. 1 shows synthesis path of linkage using Click-IT chemistry using the lytic peptide KAFKKAFKAFK-KAFKAFK (SEQ ID NO:1).

Compositions and methods are disclosed for targeted treatment of cancer or cancer-stem cells expressing a tumor associated antigen (TAA), such as toll like receptor-9 (TLR9), CD33, EGF-R, HER2, CD19, CD123, and BCMA. In some embodiments, anti-TAA binding agent, such as antibodies or ligands, are conjugated to lytic peptides disclosed herein, e.g. using a bivalent linker disclosed herein.

Anti-TAA Binding Agent

In some embodiments, the anti-TAA binding agent is single chain variable fragment (scFv) antibody. The affinity/specificity of an anti-TAA scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3). In some cases, the anti-TAA binding agent is an affinity maturated scFv. In some cases, the anti-TAA has a dissociation constant ($K_D$) for the TAA that is less than 50 nM, 40 nM, 30 nM, 25 nM, 20 nM, 15 nM, or 10 nM.

In some embodiments, the anti-TAA binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Tumor antigens are proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated. Tumor antigens are well known in the art and include, for example, a glioma-associated antigen, carcinoembryonic antigen (CEA), EGFRvIII, IL-IIRa, IL-13Ra, EGFR, FAP, B7H3, Kit, CA LX, CS-1, MUC1, BCMA, bcr-abl, HER2, β-human chorionic gonadotropin, alphafetoprotein (AFP), ALK, CD19, CD123, cyclin BI, lectin-reactive AFP, Fos-related antigen 1, ADRB3, thyroglobulin, EphA2, RAGE-1, RUI, RU2, SSX2, AKAP-4, LCK, OY-TESI, PAX5, SART3, CLL-1, fucosyl GM1, GloboH, MN-CA IX, EPCAM, EVT6-AML, TGSS, human telomerase reverse transcriptase, plysialic acid, PLAC1, RUI, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LAGE-la, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFR-beta, survivin and telomerase, legumain, HPV E6,E7, sperm protein 17, SSEA-4, tyrosinase, TARP, WT1, prostate-carcinoma tumor antigen-1 (PCTA-1), ML-IAP, MAGE, MAGE-A1, MAD-CT-1, MAD-CT-2, MelanA/ MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, CD33, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRC5D, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIll, IL-13Ra, CD123, CD19, CD33, BCMA, GD2, CLL-1, CA-IX, MUCI, HER2, and any combination thereof.

Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, pl85erbB2, p180erbB-3, c-met, nm-23H1, PSA, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCASI, SDCCAG1 6, TA-90\Mac-2 binding protein\cyclophilm C-associated protein, TAAL6, TAG72, TLP, TPS, GPC3, MUC16, LMP1, EBMA-1, BARF-1, CS1, CD319, HER1, B7H6, L1CAM, IL6, and MET.

TLR9 Targeting Ligand

Figure 4:
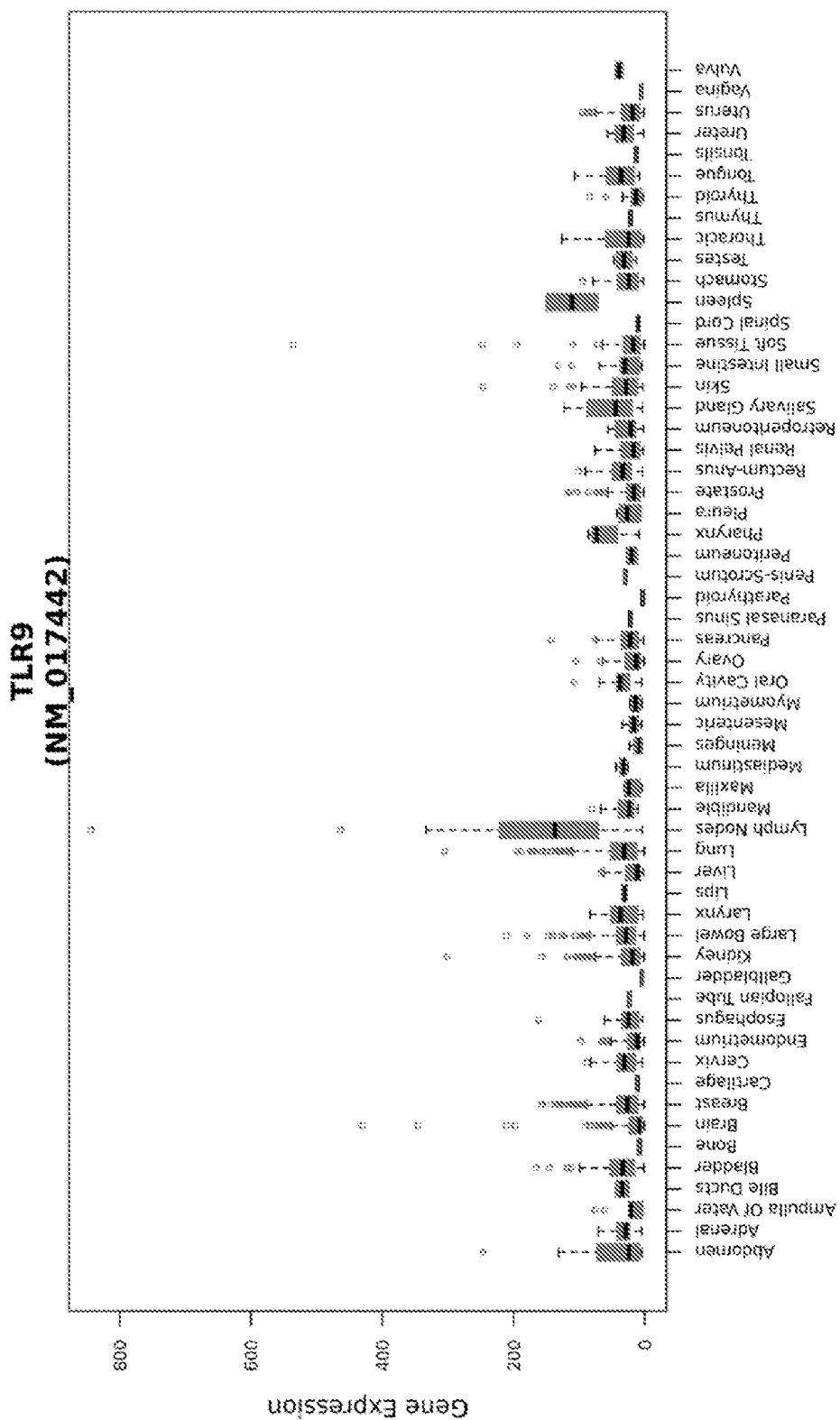
FIG. 4 is a box plot showing TLR9 overexpression in a variety of tumors. The box plot represents the 25th to 75th percentile (the box) with the median represented by the black line in the box. The outliers are in circles represent the median absolute deviation (2 SD is about the same).
Figure 5:
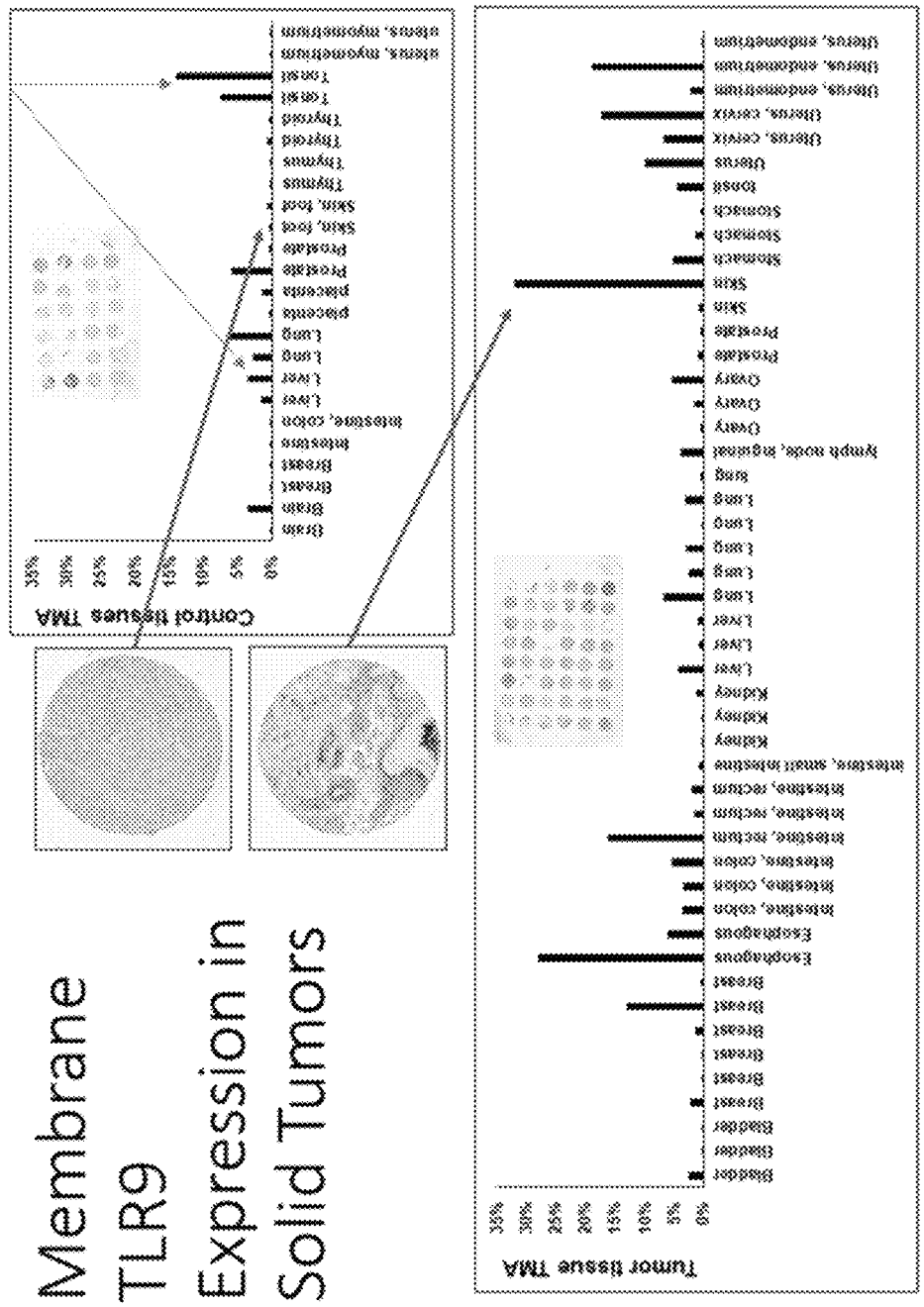
FIG. 5 shows results of tissue microarray (TMA) slides being stained with anti-TLR9 antibody. The top graph shows the tabulated data for the cores in the control TMA and a representative picture from one of the cores demonstrating the lack of brown coloration. The only positive core in that slide was inflamed tonsils which serve as a positive control. The second graph shows the tabulated results from the multi-tumor TMA (48 cases of 15 cancers) showing varied levels of TLR9 positive staining. The picture represents the core for a melanoma case that had heavy brown staining as a representative figure.
Figure 6:
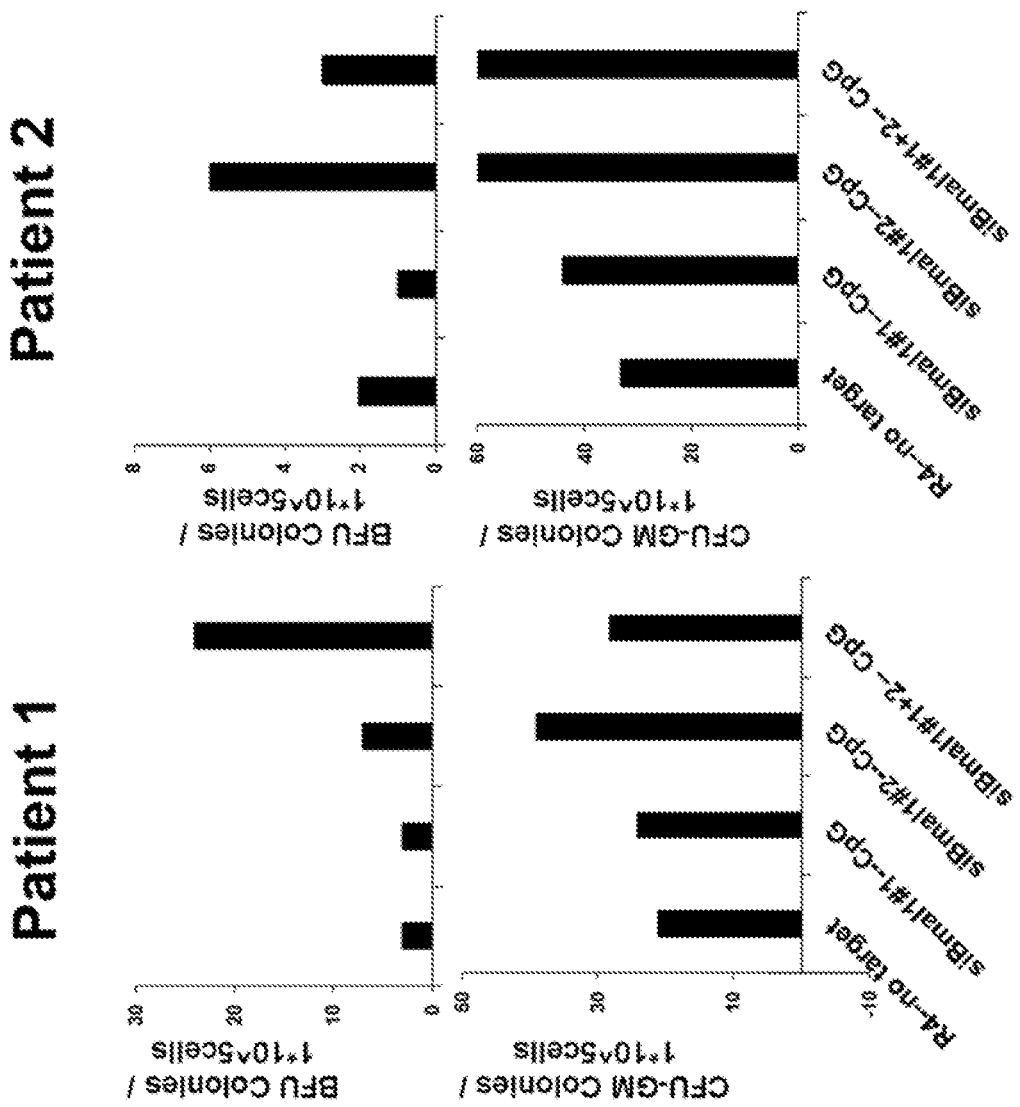
FIG. 6 shows two separate MDS BM primary specimens were treated with CpG conjugated with siRNA targeting Bmal1 sequences 1 and 2 (two different sequences) or their combination, cultured for 48 hours before reculturing in methylcellulose media supplemented with growth factors for 14 days. At that point hematopoietic colonies were counted for BFU-E and CFU-GM.
Figure 7:
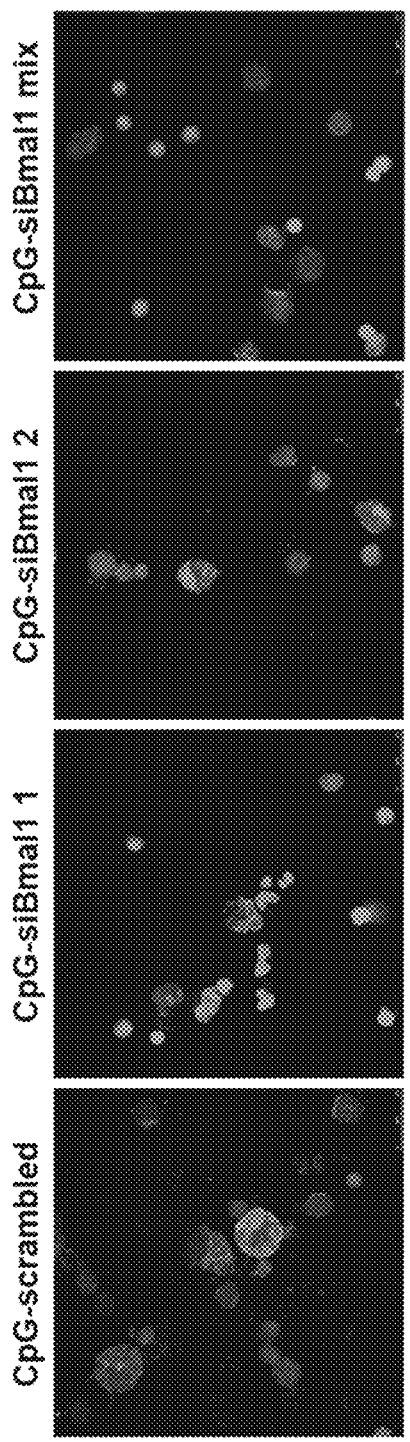
FIG. 7 shows an MDS BM primary specimen was treated with CpG conjugated with siRNA targeting Bmal1 sequences 1 and 2 (two different sequences) or their combination, cultured for 48 hours before cytospinning into a slide. Cells were then stained for Bmal1 expression and DAPI for nuclear staining. Slides were pictured in a confocal microscope.
Figure 8:
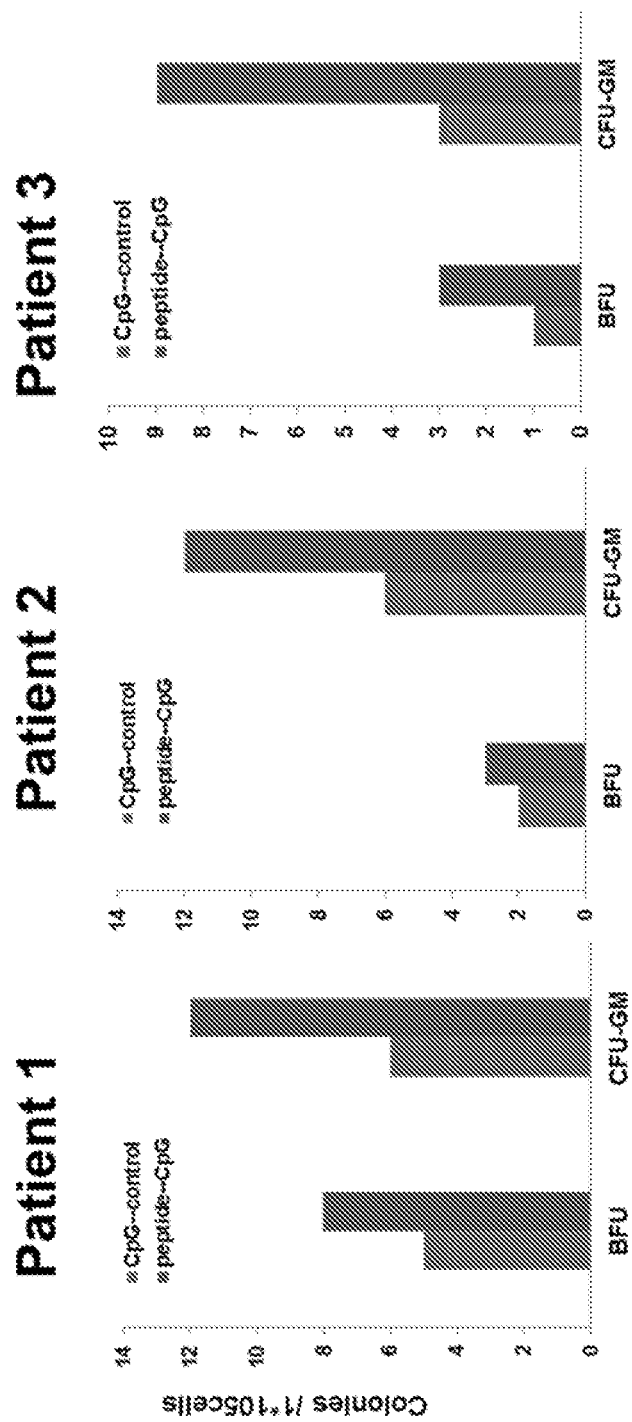
FIG. 8 shows three separate MDS BM primary specimens were treated with CpG conjugated with lytic peptide, cultured for 48 hours before reculturing in methylcellulose media supplemented with growth factors for 14 days. At that point hematopoietic colonies were counted for BFU-E and GFU-GM.
Figures 9A, 9B, 9C:
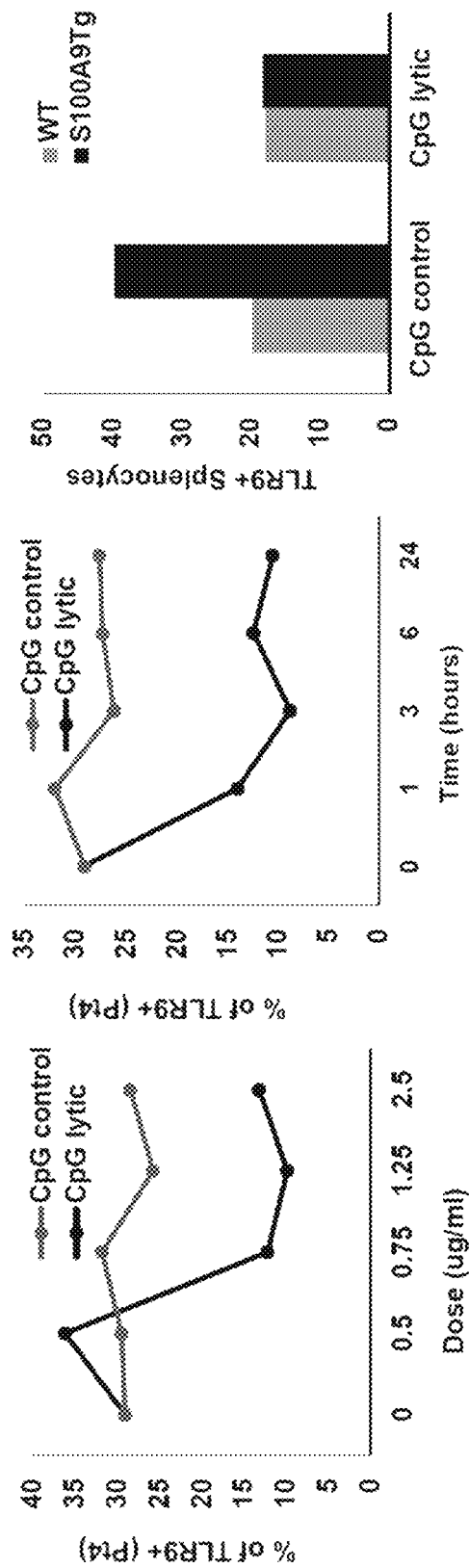
FIGS. 9A and 9B show CpG-lytic peptide acts effectively at a low dose (FIG. 9A) and with quick sustained response (FIG. 9B) ex vivo in a primary patient bone marrow.
FIG. 9C shows reduction of overexpressing TLR9+ cells in wildtype and S100A9Tg mice without affecting basal levels of normal cells.
Figure 10:
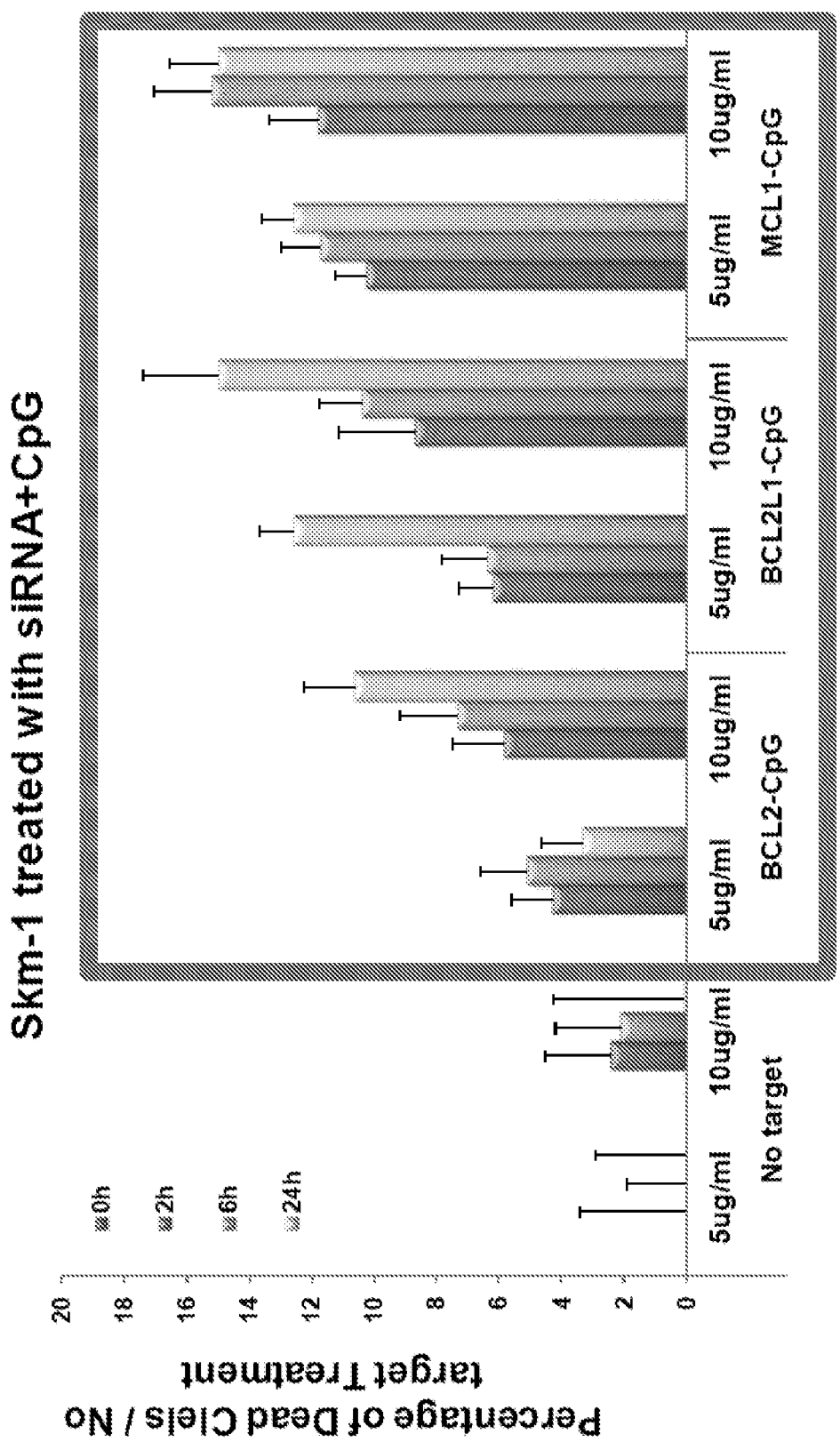
FIG. 10 shows the effectiveness of CpG-siRNA constructs (BCL2, BCL-XL and MCL1) using SKM1, a cell line derived from an MDS patient which has high surface TLR9 expression.
Figure 11:
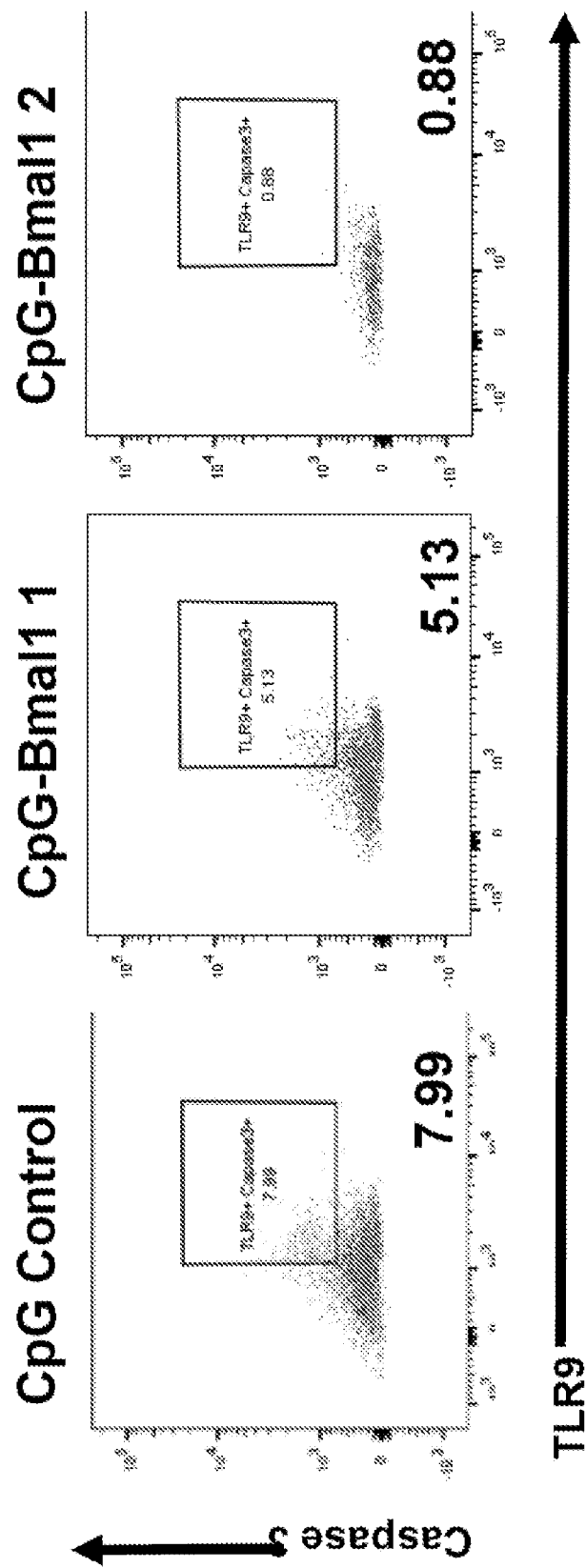
FIG. 11 shows targeting of Bmal1 by CpG-siRNA also reduced the proportion of surface TLR9+ cells in a primary specimen.

In some cases, the TAA is TLR9. Therefore, disclosed are compositions and methods for targeting TLR9-expressing cancers, such as primary human MDS hematopoietic stem and progenitor cells (HSPC). FIG. 4 identifies other cancers, such as lung and breast cancers, that have increased TLR9 expression. FIG. 5 shows TLR9 protein expression in a variety of tumor tissues. For example, cancers of the skin, esophagus, colon, rectum, liver, lung, and uterus have been shown to have increased TLR9 protein expression.

In particular, molecules containing TLR9 targeting ligands that target cytotoxic agents to TLR9-expressing malignant cells are disclosed. Therefore, the molecule can comprise a TLR9 targeting ligand ("TTL") and a lytic peptide disclosed herein. For example, the TTL and cytotoxic agent can be joined by a bivalent linker. In some embodiments, the molecule comprises a TTL conjugated to any payload, such as a diagnostic or therapeutic agent, via a bivalent linker disclosed herein. Non-limiting examples of payloads include therapeutic and diagnostic agents. For example, therapeutic agents include cytotoxic compounds, lytic peptides, cationic toxic lipid moieties, radioactive isotypes, or other chemical compounds.

The TTL can in some embodiments be a CpG oligodeoxynucleotide, such as an unmethylated CpG oligodeoxynucleotide, or an analogue or derivative thereof that binds TLR9. CpG oligodeoxynucleotides (or CpG ODN) are short single-stranded synthetic DNA molecules that contain a cytosine triphosphate deoxynucleotide followed by a guanine triphosphate deoxynucleotide. The "p" refers to the phosphodiester link between consecutive nucleotides, although some ODN have a modified phosphorothioate (PS) backbone instead. When these CpG motifs are unmethylated, they act as immunostimulants. CpG motifs are considered pathogen-associated molecular patterns (PAMPs) due to their abundance in microbial genomes but their rarity in vertebrate genomes. The CpG PAMP is recognized by the pattern recognition receptor (PRR) Toll-Like Receptor 9 (TLR9), which is constitutively expressed internally only in B cells and plasmacytoid dendritic cells (pDCs) in humans and other higher primates. However, extracellular expression of this receptor only happens in certain pathologies. Moreover, MDS progenitors, and in particular MDS stem cells (HSC), overexpress Toll-like receptor (TLR)-9 extracellularly, permitting development of a targeting approach using unmethylated CpG oligonucleotides linked to bioactive payloads for cellular delivery.

Synthetic CpG ODN differ from microbial DNA in that they have a partially or completely phosphorothioated (PS) backbone instead of the typical phosphodiester backbone and a poly G tail at the 3' end, 5' end, or both. PS modification protects the ODN from being degraded by nucleases such as DNase in the body and poly G tail enhances cellular uptake. The poly G tails form intermolecular tetrads that result in high molecular weight aggregates. Numerous sequences have been shown to stimulate TLR9 with variations in the number and location of CpG dimers, as well as the precise base sequences flanking the CpG dimers. This led to the creation of five unofficial classes or categories of CpG ODN based on their sequence, secondary structures, and effect on human peripheral blood mononuclear cells (PBMCs). The five classes are Class A (Type D), Class B (Type K), Class C, Class P, and Class S.

In some embodiments, the TTL comprises an antibody. The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

Bivalent Linker

The bivalent linker can be any molecule suitable to link a compound, polypeptide, or nucleic acid to a TTL (e.g., CpG ODN). Methods and compositions for conjugating biomolecules, such as polynucleotides, are disclosed in G. T. Hermanon, Bioconjugate Techniques ($2^{nd}$ ed.), Academic Press (2008), which is incorporated by reference in its entirety for the teaching of these techniques.

In some embodiments, the bivalent linker is a non-nucleotidic linker. As used herein, the term "non-nucleotidic" refers to a linker that does not include nucleotides or nucleotide analogs. Typically, non-nucleotidic linkers comprise an atom such as oxygen or sulfur, a unit such as C(O), C(O)NH, SO, $SO_2$, $SO_2NH$, or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, SS, S(O), $SO_2$, $N(R^1)_2$, $NR^1$, C(O), C(O)O, C(O)NH, —$OPO_2O$—, cleavable linking group, substituted or unsubstituted aryl, substituted or unsubstituted heteroaryl, substituted or unsubstituted heterocyclic; where R' is hydrogen, acyl, aliphatic or substituted aliphatic.

In some embodiments, the bivalent linker comprises at least one cleavable linking group, i.e. the linker is a cleavable linker. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In some embodiments, a cleavable linker can be used to release the linked components after transport to the desired target. The intended nature of the conjugation or coupling interaction, or the desired biological effect, will determine the choice of linker group. For example, the bivalent linker can comprise a photocleavable PC linker. In some embodiments, the oligonucleotide is cleavable by dicer to produce isolate individual siRNA from the oligonucleotide.

Additional examples of linkers include Hexanediol, Spacer 9, Spacer 18, 1',2'-Dideoxyribose (dSc), and I-Linker.

In some embodiments, the linker comprises m-Maleimidobenzyol-N-hydroxysuccinimide ester (MBS), Sulfo-m-maleimidobenzyol-N-hydroxysuccinimide ester (sulfo-MBS), or Sulfosuccinimidyl-4-(N-maleimidomethyl)cyclohexane-1-carboxylate (SMCC).

Figure 2:
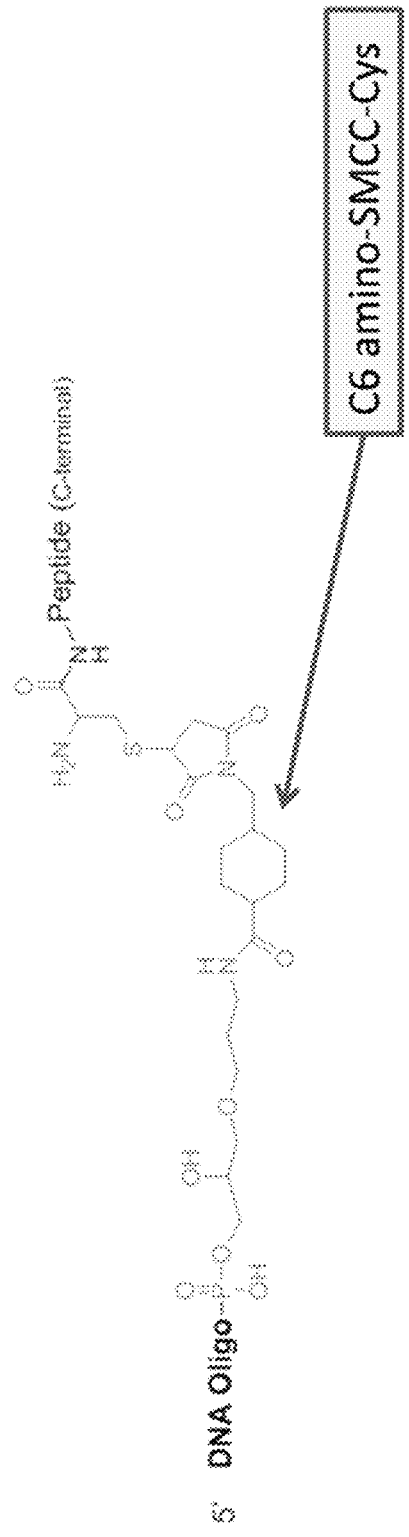
FIG. 2 shows sequences of a phosphorothioated CpG linked and peptide sequences and C6 amino-SMCC-Cys linker strategy. The illustrated TLR9 ligand for both peptides is the CpG sequence T*C*C*A*T*G*A*C*G*T*T*C*C*T*G*A*T*G*C*T* (SEQ ID N0:14, *=phosphorothioate). The illustrated lytic peptide is KAFKKAFKAFK-KAFKAFK (SEQ ID NO:1). The illustrated scrambled control is KFKFKFKAAKFAAAKFKK (SEQ ID NO: 65).

In some embodiments, the linker is a C6 amino-SMCC-Cys linker as shown in FIG. 2.

In some embodiments, the linker is produced using click chemistry reactions, as shown in FIG. 1. The cock chemistry approach was originally conceived as a method to rapidly generate complex substances by joining small subunits together in a modular fashion. Various forms of click chemistry reaction are known in the art, such as the Huisgen 1,3-dipolar cycloaddition copper catalyzed reaction, which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

Cytotoxic Agent

The cytotoxic agent of the disclosed compositions can be any agent capable of killing a cancer cell, e.g., when internalized by the cell. For example, the cytotoxic agent may be a cytotoxic peptide (e.g., lytic peptide) or a radionuclide. Suitable cytotoxins are known to those skilled in the art and include plant and bacterial toxins, such as, abrin, alpha toxin, diphtheria toxin, exotoxin, gelonin, pokeweed antiviral protein, ricin, and saporin.

Many natural and synthetic peptides and proteins having cytolytic activity are known. Cytolytic peptides are also described as pore-forming peptides or cytolysins. Interactions of pore forming peptides with the surface of the membrane may be based on nonspecific electrostatic interactions of the positively charged peptide with negatively charged surface of cell membrane. These peptides are generally of cationic character, so that they are capable of electrostatic interactions with surfaces with predominantly negatively charged particles. Upon contact and interaction of a cytolytic peptide with lipids on the cell surface, and after penetration inside the cell with the lipids on the surface of the mitochondrial membrane, interruption of the continuity of the cell membrane occurs, followed by formation of small size transmembrane pores, by which leakage of the contents of the cytoplasm, including ions, outside the cell occurs, resulting in rapid and irreversible electrolyte imbalance in the cell, cell lysis and death. The interactions of pore-forming peptides with the surface of the membrane may also include interactions with specific receptors present on the surface.

Naturally occurring cytolytic peptides of bacterial, plant or mammalian origin capable of forming pores include cecropin A and B, aurein 1.2, citropin 1.1, defensin (HNP-2), lactoferricin B, tachyplesin, PR-39, cytolysins of *Enterococcus faecalis*, delta hemolysin, diphtheria toxin, cytolysin of *Vibrio cholerae*, toxin from *Actinia equina*, granulysin, lytic peptides from *Streptococcus intermedius*, lentiviral lytic peptides, leukotoxin of *Actinobacillus actinomycetemcomitans*, magainin, melittin, lymphotoxin, enkephalin, paradaxin, perforin (in particular the N-terminal fragment thereof), perfringolysin 0 (PFO/theta toxin) from *Clostridium perfringens*, and streptolysins.

There are also known synthetic cytolytic pore-forming peptides. They are often hybrids of natural cytolytic peptides fragments, such as a hybrid of a cecropin A fragment and a magainin 2 fragment or a hybrid of a cecropin A fragment and a melittin fragment. Other well-known cytolytic synthetic peptides are described, for example, in Regen et al., Biochem. Biophys. Res. Commun. (199) 159:566-571, which is incorporated by reference for these peptides.

In some embodiments, the lytic peptide comprises the amino acid sequence KAFKKAFKAFKKAFKAFK (SEQ ID NO:1). In some embodiments, the lytic peptide function is attributable to the alternating positively and negatively charged amino acids. Therefore, in some embodiments, the lytic peptide comprises the amino acid sequence PHHP-PHHPHHPPHHPHHP (SEQ ID NO:2), where P is a positively charged amino acid and H is a hydrophobic amino acid. In some embodiments, the lytic peptide comprise an amino acid sequence that has at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to the amino acid sequence SEQ ID NO:2, or a fragment thereof of at least 12, 13, 14, 15, 16, or 17 amino acids in length.

In some embodiment, the lytic peptide comprises an amino acid sequence selected from the group consisting of KIKMVISWKG (SEQ ID NO:18; HYD1); AIAMVISWAG (SEQ ID NO:19; HYDE); AIKMVISWAG (SEQ ID NO:20; HYDE); AIKMVISWKG (SEQ ID NO:21; HYD2); AKMVISW (SEQ ID NO:22); AKMVISWKG (SEQ ID NO:23); IAMVISW (SEQ ID NO:24); IAMVISWKG (SEQ ID NO:25); IKAVISW (SEQ ID NO:26); IKAVISWKG (SEQ ID NO: 27); IKMAISW (SEQ ID NO:28); IKMAISWKG (SEQ ID NO:29); IKMVASW (SEQ ID NO:30); IKMVASWKG (SEQ ID NO:31); IKMVIAW (SEQ ID NO:32); IKMVIAWKG (SEQ ID NO:33); IKMVISA (SEQ ID NO:34); IKMVISAKG (SEQ ID NO:35); IKMVISW (SEQ ID NO:36); IKMVISWAG (SEQ ID NO:37); KMVISWKA (SEQ ID NO:38); IKMVISWKG (SEQ ID NO:39; HYD1 8; (—K)HYDI); ISWKG (SEQ ID NO:40); KAKMVISWKG (SEQ ID NO:41); KIAMVISWAG (SEQ ID NO:42; HYD7); KIAMVISWKG (SEQ ID NO:43); KIKAVISWKG (SEQ ID NO:44); KIK-MAISWKG (SEQ ID NO:45); KIKMV (SEQ ID NO:46); KIKMVASWKG (SEQ ID NO:47); KIKMVI (SEQ ID NO:48; HYDI 6); KIKMVIA WKG (SEQ ID NO:49); KIKMVIS (SEQ ID NO:50; HYDI 5); KIKMVISAKG (SEQ ID NO:51); KIKMVISW (SEQ ID NO:52; HYD14); KIKMVISWAG (SEQ ID NO:53); KIKMVISWK (SEQ ID NO:54; HYD17; HYDI(-G)); KIKMVISWKA (SEQ ID NO:55); KMVISWKG (SEQ ID NO:56; HYD9); LSWKG (SEQ ID NO:57; HYD12); MVISWKG (SEQ ID NO:58; HYDIO); SWKG (SEQ ID NO:59; HYD13); VISWKG (SEQ ID NO:60; HYDI I); WIKSMKIVKG (SEQ ID NO:61); KMVIXW (SEQ ID NO:62); IKMVISWXX (SEQ ID NO:63); and KMVISWXX (SEQ ID NO:64); wherein X is any amino acid (traditional or non-traditional amino acid). In another embodiment, the peptide consists of the identified amino acid sequence. In another embodiment, the peptide consists essentially of the identified amino acid sequence. The lytic peptide can comprise at least one D-amino acid. In some cases, each amino acid of the peptide is a D-amino acid.

In some embodiments, the cytotoxic agent is a pyrrolobenzodiazepine (PBD). Pyrrolobenzodiazepines (PBDs) are known in the art, some of which have the ability to recognise and bond to specific sequences of DNA. PBDs are of the general structure:

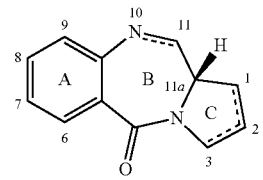

They differ in the number, type and position of substituents, in both their aromatic A rings and pyrrolo C rings, and in the degree of saturation of the C ring. In the B-ring there is either an imine (N═C), a carbinolamine (NH—CH(OH)), or a carbinolamine methyl ether (NH—CH(OMe)) at the N10-C11 position which is the electrophilic center responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, InAntibiotics III. Springer-Verlag, New York, pp. 3-11 (1975); Hurley and Needham-VanDevanter, Acc. Chem. Res., 19, 230-237 (1986)). Their ability to form an adduct in the minor groove, enables them to interfere with DNA processing.

In some embodiments, the cytotoxic agent is a functional nucleic acid, such as one that inhibits anti-apoptotic gene targets (e.g., Bcl-2, Bcl-xL, and Mcl-1), or promotes apoptotic gene targets (e.g., Bax, Bak, and Bcl-xS).

Functional nucleic acid molecules can be divided into the following categories, which are not meant to be limiting. For example, functional nucleic acids include antisense molecules, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$. A representative sample of methods and techniques which aid in the design and use of antisense molecules can be found in U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule (U.S. Pat. No. 5,543,293). It is preferred that the aptamer have a $K_d$ with the target molecule at least 10, 100, 1000, 10,000, or 100,000 fold lower than the $K_d$ with a background binding molecule. It is preferred when doing the comparison for a polypeptide for example, that the background molecule be a different polypeptide. Representative examples of how to make and use aptamers to bind a variety of different target molecules can be found in U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203; International Patent Application Nos. WO 9858058 by Ludwig and Sproat, WO 9858057 by Ludwig and Sproat, and WO 9718312 by Ludwig and Sproat) hairpin ribozymes (for example, U.S. Pat. Nos. 5,631,115, 5,646,031, 5,683,902, 5,712,384, 5,856,188, 5,866,701, 5,869,339, and 6,022,962), and tetrahymena ribozymes (for example, U.S. Pat. Nos. 5,595,873 and 5,652,107). There are also a number of ribozymes that are not found in natural systems, but which have been engineered to catalyze specific reactions de novo (for example, U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$. Representative examples of how to make and use triplex forming molecules to bind a variety of different target molecules can be found in U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, Science 238:407-409 (1990)).

Similarly, eukaryotic EGS/RNAse P-directed cleavage of RNA can be utilized to cleave desired targets within eukarotic cells. (Yuan et al., Proc. Natl. Acad. Sci. USA 89:8006-8010 (1992); WO 93/22434 by Yale; WO 95/24489 by Yale; Yuan and Altman, EMBO J 14:159-168 (1995), and Carrara et al., Proc. Natl. Acad. Sci. (USA) 92:2627-2631 (1995)). Representative examples of how to make and use EGS molecules to facilitate cleavage of a variety of different target molecules be found in U.S. Pat. Nos. 5,168,053, 5,624,824, 5,683,873, 5,728,521, 5,869,248, and 5,877,162.

Gene expression can also be effectively silenced in a highly specific manner through RNA interference (RNAi). This silencing was originally observed with the addition of double stranded RNA (dsRNA) (Fire, A., et al. (1998) Nature, 391:806-11; Napoli, C., et al. (1990) Plant Cell 2:279-89; Hannon, G. J. (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit. Disclosed herein are any siRNA designed as described above based on the sequences for anti-apoptotic Bcl-2 member proteins, e.g., Bcl-2, Bcl-xL, and Mcl-1.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. Disclosed herein are any shRNA designed as described above based on the sequences for the herein disclosed inflammatory mediators.

In some embodiments, the disclosed molecule comprises a plurality of cytotoxic agents linked to each targeting agent. For example, the molecule can comprise 1, 2, 3, 4, 5, 6, 7, 8, 9, 10, or more cytotoxic agents linked directly or indirectly to the targeting agent.

Pharmaceutical Composition

Also disclosed is a pharmaceutical composition comprising a molecule disclosed herein in a pharmaceutically acceptable carrier. Pharmaceutical carriers are known to those skilled in the art. These most typically would be standard carriers for administration of drugs to humans, including solutions such as sterile water, saline, and buffered solutions at physiological pH. For example, suitable carriers and their formulations are described in Remington: The Science and Practice of Pharmacy (21 ed.) ed. PP. Gerbino, Lippincott Williams & Wilkins, Philadelphia, Pa. 2005. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. The solution should be RNAse free. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers dextrose, dextrose and sodium chloride, lactated Ringers, or fixed oils. Intravenous vehicles include fluid and nutrient replenishers, electrolyte replenishers (such as those based on Ringers dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Methods of Treatment

Also disclosed is a method for treating a TLR9-expressing cancer, such as a myelodysplastic syndrome (MDS), in a subject by administering to the subject a therapeutically effective amount of the disclosed pharmaceutical composition. The method can further involve administering to the subject lenalidomide, or an analogue or derivative thereof. FIG. 4 identifies other cancers, such as lung and breast cancers, that have increased TLR9 expression. FIG. 5 shows TLR9 protein expression in a variety of tumor tissues. For example, cancers of the skin, esophagus, colon, rectum, liver, lung, and uterus have been shown to have increased TLR9 protein expression.

A representative but non-limiting list of cancers include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

In some cases, the method further involves assaying a biopsy sample from the subject for TLR9 expression prior to treatment. This can be done using routine methods, such as immunodetection methods. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for a cancer expressing a disclosed tumor antigen, such as a TLR9-expressing cancer. Thus, the method can further comprise identifying a subject at risk for the cancer, such as a TLR9-expressing cancer, prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. A typical daily dosage of the disclosed composition used alone might range from about 1 µg/kg to up to 100 mg/kg of body weight or more per day, depending on the factors mentioned above.

In some embodiments, the molecule is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of molecule administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

Definitions

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "CpG motif" refers to a nucleotide sequence, which contains unmethylated cytosine-guanine dinucleotide linked by a phosphate bond.

The term "CpG oligodeoxynucleotide" or "CpG ODN" refers to an oligodeoxynucleotide comprising at least one CpG motif and that binds TLR9.

A "fusion protein" or "fusion polypeptide" refers to a hybrid polypeptide which comprises polypeptide portions from at least two different polypeptides. The portions may be from proteins of the same organism, in which case the fusion protein is said to be "intraspecies", "intragenic", etc. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. A first polypeptide may be fused to the N-terminus, the C-terminus, or the N- and C-terminus of a second polypeptide. Furthermore, a first polypeptide may be inserted within the sequence of a second polypeptide.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "isolated polypeptide" refers to a polypeptide, which may be prepared from recombinant DNA or RNA, or be of synthetic origin, some combination thereof, or which may be a naturally-occurring polypeptide, which (1) is not associated with proteins with which it is normally associated in nature, (2) is isolated from the cell in which it normally occurs, (3) is essentially free of other proteins from the same cellular source, (4) is expressed by a cell from a different species, or (5) does not occur in nature.

The term "isolated nucleic acid" refers to a polynucleotide of genomic, cDNA, synthetic, or natural origin or some combination thereof, which (1) is not associated with the cell in which the "isolated nucleic acid" is found in nature, or (2) is operably linked to a polynucleotide to which it is not linked in nature.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "nucleic acid" refers to a polymeric form of nucleotides, either ribonucleotides or deoxyribonucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "protein" (if single-chain), "polypeptide" and "peptide" are used interchangeably herein when referring to a gene product, e.g., as may be encoded by a coding sequence. When referring to "polypeptide" herein, a person of skill in the art will recognize that a protein can be used instead, unless the context clearly indicates otherwise. A "protein" may also refer to an association of one or more polypeptides. By "gene product" is meant a molecule that is produced as a result of transcription of a gene. Gene products include RNA molecules transcribed from a gene, as well as proteins translated from such transcripts.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

A number of embodiments of the invention have been described. Nevertheless, it will be understood that various modifications may be made without departing from the spirit and scope of the invention. Accordingly, other embodiments are within the scope of the following claims.

A number of embodiments of the invention have been described. Nevertheless, it will be understood that various modifications may be made without departing from the spirit and scope of the invention. Accordingly, other embodiments are within the scope of the following claims.

EXAMPLES

Example 1

With the purpose of using the high surface expression of the receptor TLR9 in the surface of stem cells, CpG, a cognate danger-associated molecular pattern (DAMP) recognized by TLR9, was used as a target for internalization of an amphipatic lytic peptide capable of lysis only when internalized. This allows the targeted killing of malignant TLR9+ hematopoietic stem cells in cancer.

A CpG sequence T*C*C*A*T*G*A*C*G*T*T*C*C*-T*G*A*T*G*C*T* (SEQ ID NO:14) modified with thioate linkages (*=phosphorothioate linkage) was used. The initial attempt was by linking the CpG and the lytic peptide through the use of a Click-It reaction as demonstrated in FIG. 1. However, this reaction might be less stable, even though the initial reaction performed with CpG-lytic prepared this way has already shown effectivity in reducing TLR9+ stem cells. The second strategy involved the use of a C6 amino-SMCC-Cys linker as shown in FIG. 2. The CpG sequence is fully phosphothioated in order to increase stability of the CpG moiety.

Figure 3:
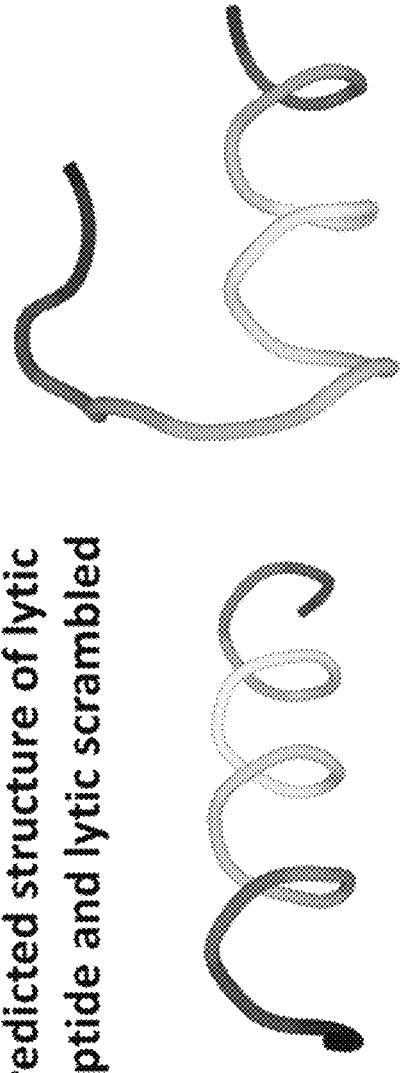
FIG. 3 shows example lytic peptide 3D structure (SEQ ID NO:1) and structure of scrambled control (SEQ ID NO: 65) used.

FIG. 2 also shows the sequence of a new lytic peptide and a scrambled sequence that was used as control. An important thing to note is that the sequence itself is important, because of the amphitatic nature of the residues, but its main function relies on the helical conformation of the peptide. Hence, as a control the same sequence of peptides was used but was looped through a 3D structure predictor until a scrambled sequence was found were the helical structure was disrupted (FIG. 3).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A molecule comprising a toll like receptor-9 (TLR9) targeting ligand conjugated to a lytic peptide via a bivalent linker, wherein the lytic peptide comprises the amino acid sequence PHHPPHHPHHPPHHPHHP (SEQ ID NO:2), wherein P is a positively charged amino acid and H is a hydrophobic amino acid, wherein the TLR9 targeting ligand is an unmethylated CpG oligodeoxynucleotide.

2. The molecule of claim 1, wherein the lytic peptide comprises the amino acid sequence SEQ ID NO:1.

3. A pharmaceutical composition comprising the molecule of claim 1 in a pharmaceutically acceptable carrier.

4. A method for treating a cancer in a subject, comprising administering to the subject in need thereof a therapeutically effective amount of the pharmaceutical composition of claim 3, wherein the cancer comprises a myelodysplastic syndrome (MDS).

5. The method of claim 4, further comprising assaying a biopsy sample from the subject for TLR9 expression prior to treatment.

* * * * *

SEQUENCE LISTING

```
<160> NUMBER OF SEQ ID NOS: 65

<210> SEQ ID NO 1
<211> LENGTH: 18
<212> TYPE: PRT
<213> ORGANISM: Artificial Sequence
<220> FEATURE:
<223> OTHER INFORMATION: Synthetic Construct

<400> SEQUENCE: 1

Lys Ala Phe Lys Lys Ala Phe Lys Ala Phe Lys Lys Ala Phe Lys Ala
1               5                   10                  15

Phe Lys

<210> SEQ ID NO 2
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Postive charge amino acid
<220> FEATURE:
<221> NAME/KEY: MISC_FEATURE
<222> LOCATION: (2)..(3)
<223> OTHER INFORMATION: hydrophobic amino acid
<220> FEATURE:
<221> NAME/KEY: MISC_FEATURE
<222> LOCATION: (4)..(5)
<223> OTHER INFORMATION: Postive charge amino acid
<220> FEATURE:
<221> NAME/KEY: MISC_FEATURE
<222> LOCATION: (6)..(7)
<223> OTHER INFORMATION: hydrophobic amino acid
<220> FEATURE:
<221> NAME/KEY: MISC_FEATURE
<222> LOCATION: (8)..(8)
<223> OTHER INFORMATION: Postive charge amino acid
<220> FEATURE:
<221> NAME/KEY: MISC_FEATURE
<222> LOCATION: (9)..(10)
<223> OTHER INFORMATION: hydrophobic amino acid
<220> FEATURE:
<221> NAME/KEY: MISC_FEATURE
<222> LOCATION: (11)..(12)
<223> OTHER INFORMATION: Postive charge amino acid
<220> FEATURE:
<221> NAME/KEY: MISC_FEATURE
<222> LOCATION: (13)..(14)
```

```
<223> OTHER INFORMATION: hydrophobic amino acid
<220> FEATURE:
<221> NAME/KEY: MISC_FEATURE
<222> LOCATION: (15)..(15)
<223> OTHER INFORMATION: Postive charge amino acid
<220> FEATURE:
<221> NAME/KEY: MISC_FEATURE
<222> LOCATION: (16)..(17)
<223> OTHER INFORMATION: hydrophobic amino acid
<220> FEATURE:
<221> NAME/KEY: MISC_FEATURE
<222> LOCATION: (18)..(18)
<223> OTHER INFORMATION: Postive charge amino acid

<400> SEQUENCE: 2

Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
tccatgacgt tcctgatgct                                           20

<210> SEQ ID NO 4
<211> LENGTH: 24
<212> TYPE: DNA
<213> ORGANISM: Artificial Sequence
<220> FEATURE:
<223> OTHER INFORMATION: Synthetic Construct

<400> SEQUENCE: 4
tcgtcgtttt gtcgttttgt cgtt                                      24

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
tccatgacgt tcctgacgtt                                           20

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
ggggacgacg tcgtgggggg g                                         21

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
```
gggggacgat cgtcgggggg                    20

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct

<400> SEQUENCE: 8
tcgtcgttgt cgttttgtcg tt                 22

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct

<400> SEQUENCE: 9
tcgacgttcg tcgttcgtcg ttc                23

<210> SEQ ID NO 10
<211> LENGTH: 26
<212> TYPE: DNA
<213> ORGANISM: Artificial Sequence
<220> FEATURE:
<223> OTHER INFORMATION: Synthetic Construct

<400> SEQUENCE: 10
tcgcgacgtt cgcccgacgt tcggta             26

<210> SEQ ID NO 11
<211> LENGTH: 22
<212> TYPE: DNA
<213> ORGANISM: Artificial Sequence
<220> FEATURE:
<223> OTHER INFORMATION: Synthetic Construct

<400> SEQUENCE: 11
tcgtcgtttt cggcgcgcgc cg                 22

<210> SEQ ID NO 12
<211> LENGTH: 25
<212> TYPE: DNA
<213> ORGANISM: Artificial Sequence
<220> FEATURE:
<223> OTHER INFORMATION: Synthetic Construct

<400> SEQUENCE: 12
tcgtcgtcgt tcgaacgacg ttgat              25

<210> SEQ ID NO 13
<211> LENGTH: 29
<212> TYPE: DNA
<213> ORGANISM: Artificial Sequence
<220> FEATURE:
<223> OTHER INFORMATION: Synthetic Construct

<400> SEQUENCE: 13
tcgcgaacgt tcgccgcgtt cgaacgcgg          29

<210> SEQ ID NO 14
<211> LENGTH: 20
<212> TYPE: DNA
<213> ORGANISM: Artificial Sequence

```
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: Phophorothioate bond

<400> SEQUENCE: 14
tccatgacgt tcctgatgct                                                   20

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: Phosphorothioate bond
<220> FEATURE:
<221> NAME/KEY: misc_feature
<222> LOCATION: (16)..(21)
<223> OTHER INFORMATION: Phosphorothioate bond

<400> SEQUENCE: 15
ggggacgacg tcgtgggggg g                                                 21

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Phosphorothioate bond
<220> FEATURE:
<221> NAME/KEY: misc_feature
<222> LOCATION: (15)..(20)
<223> OTHER INFORMATION: Phosphorothioate bond

<400> SEQUENCE: 16
gggggacgat cgtcggggggg                                                  20

<210> SEQ ID NO 17
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(25)
<223> OTHER INFORMATION: Phosphorothioate bond

<400> SEQUENCE: 17
tcgtcgtcgt tcgaacgacg ttgat                                             25

<210> SEQ ID NO 18
<211> LENGTH: 10
<212> TYPE: PRT
<213> ORGANISM: Artificial Sequence
<220> FEATURE:
<223> OTHER INFORMATION: Synthetic Construct

<400> SEQUENCE: 18

Lys Ile Lys Met Val Ile Ser Trp Lys Gly
1               5                   10
```

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Ala Ile Ala Met Val Ile Ser Trp Ala Gly
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Ala Ile Lys Met Val Ile Ser Trp Ala Gly
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Ala Ile Lys Met Val Ile Ser Trp Lys Gly
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct

<400> SEQUENCE: 22

Ala Lys Met Val Ile Ser Trp
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Ala Lys Met Val Leu Ser Trp Lys Gly
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct

<400> SEQUENCE: 24

Ile Ala Met Val Ile Ser Trp
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct

<400> SEQUENCE: 25

Ile Ala Met Val Ile Ser Trp Lys Gly
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic Construct

<400> SEQUENCE: 26

Ile Lys Ala Val Ile Ser Trp
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Ile Lys Ala Val Ile Ser Trp Lys Gly
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Construct

<400> SEQUENCE: 28

Ile Lys Met Ala Ile Ser Trp
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Ile Lys Met Ala Ile Ser Trp Lys Gly
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Ile Lys Met Val Ala Ser Trp
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

Ile Lys Met Val Ala Ser Trp Lys Gly
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic Construct

<400> SEQUENCE: 32

Ile Lys Met Val Ile Ala Trp
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

Ile Lys Met Val Ile Ala Trp Lys Gly
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34

Ile Lys Met Val Ile Ser Ala
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

<400> SEQUENCE: 35

Ile Lys Met Val Ile Ser Ala Lys Gly
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct

<400> SEQUENCE: 36

Ile Lys Met Val Ile Ser Trp
1               5

<210> SEQ ID NO 37

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 37

Ile Lys Met Val Ile Ser Trp Ala Gly
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

<400> SEQUENCE: 38

Lys Met Val Ile Ser Trp Lys Ala
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct

<400> SEQUENCE: 39

Ile Lys Met Val Ile Ser Trp Lys Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Construct

<400> SEQUENCE: 40

Ile Ser Trp Lys Gly
1               5

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Lys Ala Lys Met Val Ile Ser Trp Lys Gly
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Lys Ile Ala Met Val Ile Ser Trp Ala Gly
1               5                   10

<210> SEQ ID NO 43
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 43

Lys Ile Ala Met Val Ile Ser Trp Lys Gly
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

Lys Ile Lys Ala Val Ile Ser Trp Lys Gly
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Lys Ile Lys Met Ala Ile Ser Trp Lys Gly
1               5                   10

<210> SEQ ID NO 46
<211> LENGTH: 5
<212> TYPE: PRT
<213> ORGANISM: Artificial Sequence
<220> FEATURE:
<223> OTHER INFORMATION: Synthetic Construct

<400> SEQUENCE: 46

Lys Ile Lys Met Val
1               5

<210> SEQ ID NO 47
<211> LENGTH: 10
<212> TYPE: PRT
<213> ORGANISM: Artificial Sequence
<220> FEATURE:
<223> OTHER INFORMATION: Synthetic Construct

<400> SEQUENCE: 47

Lys Ile Lys Met Val Ala Ser Trp Lys Gly
1               5                   10

<210> SEQ ID NO 48
<211> LENGTH: 6
<212> TYPE: PRT
<213> ORGANISM: Artificial Sequence
<220> FEATURE:
<223> OTHER INFORMATION: Synthetic Construct

<400> SEQUENCE: 48

Lys Ile Lys Met Val Ile
1               5

<210> SEQ ID NO 49
<211> LENGTH: 7
<212> TYPE: PRT
```

```
<213> ORGANISM: Artificial Sequence
<220> FEATURE:
<223> OTHER INFORMATION: Synthetic Construct

<400> SEQUENCE: 49

Lys Ile Lys Met Val Ile Ala
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic Construct

<400> SEQUENCE: 50

Lys Ile Lys Met Val Ile Ser
1               5

<210> SEQ ID NO 51
<211> LENGTH: 10
<212> TYPE: PRT
<213> ORGANISM: Artificial Sequence
<220> FEATURE:
<223> OTHER INFORMATION: Synthetic Construct

<400> SEQUENCE: 51

Lys Ile Lys Met Val Ile Ser Ala Lys Gly
1               5                   10

<210> SEQ ID NO 52
<211> LENGTH: 8
<212> TYPE: PRT
<213> ORGANISM: Artificial Sequence
<220> FEATURE:
<223> OTHER INFORMATION: Synthetic Construct

<400> SEQUENCE: 52

Lys Ile Lys Met Val Ile Ser Trp
1               5

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53

Lys Ile Lys Met Val Ile Ser Trp Ala Gly
1               5                   10

<210> SEQ ID NO 54
<211> LENGTH: 9
<212> TYPE: PRT
<213> ORGANISM: Artificial Sequence
<220> FEATURE:
<223> OTHER INFORMATION: Synthetic Construct

<400> SEQUENCE: 54

Lys Ile Lys Met Val Ile Ser Trp Lys
1               5

<210> SEQ ID NO 55
<211> LENGTH: 10
<212> TYPE: PRT
<213> ORGANISM: Artificial Sequence
```

```
<220> FEATURE:
<223> OTHER INFORMATION: Synthetic Construct

<400> SEQUENCE: 55

Lys Ile Lys Met Val Ile Ser Trp Lys Ala
1               5                   10

<210> SEQ ID NO 56
<211> LENGTH: 8
<212> TYPE: PRT
<213> ORGANISM: Artificial Sequence
<220> FEATURE:
<223> OTHER INFORMATION: Synthetic Construct

<400> SEQUENCE: 56

Lys Met Val Ile Ser Trp Lys Gly
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic Construct

<400> SEQUENCE: 57

Leu Ser Trp Lys Gly
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic Construct

<400> SEQUENCE: 58

Met Val Ile Ser Trp Lys Gly
1               5

<210> SEQ ID NO 59
<211> LENGTH: 4
<212> TYPE: PRT
<213> ORGANISM: Artificial Sequence
<220> FEATURE:
<223> OTHER INFORMATION: Synthetic Construct

<400> SEQUENCE: 59

Ser Trp Lys Gly
1

<210> SEQ ID NO 60
<211> LENGTH: 6
<212> TYPE: PRT
<213> ORGANISM: Artificial Sequence
<220> FEATURE:
<223> OTHER INFORMATION: Synthetic Construct

<400> SEQUENCE: 60

Val Ile Ser Trp Lys Gly
1               5

<210> SEQ ID NO 61
<211> LENGTH: 10
<212> TYPE: PRT
<213> ORGANISM: Artificial Sequence
<220> FEATURE:
```

```
<223> OTHER INFORMATION: Synthetic Construct

<400> SEQUENCE: 61

Trp Ile Lys Ser Met Lys Ile Val Lys Gly
1               5                   10

<210> SEQ ID NO 62
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is any amino acid

<400> SEQUENCE: 62

Lys Met Val Ile Xaa Trp
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(9)
<223> OTHER INFORMATION: Xaa is any amino acid

<400> SEQUENCE: 63

Ile Lys Met Val Ile Ser Trp Xaa Xaa
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(8)
<223> OTHER INFORMATION: Xaa is any amino acid

<400> SEQUENCE: 64

Lys Met Val Ile Ser Trp Xaa Xaa
1               5

<210> SEQ ID NO 65
<211> LENGTH: 18
<212> TYPE: PRT
<213> ORGANISM: Artificial Sequence
<220> FEATURE:
<223> OTHER INFORMATION: Synthetic Construct

<400> SEQUENCE: 65

Lys Phe Lys Phe Lys Phe Lys Ala Ala Lys Phe Ala Ala Ala Lys Phe
1               5                   10                  15

Lys Lys
```